(12) United States Patent
Wedel

(10) Patent No.: US 9,050,354 B2
(45) Date of Patent: Jun. 9, 2015

(54) THERAPEUTIC ANTISENSE OLIGONUCLEOTIDE COMPOSITIONS FOR THE TREATMENT OF INFLAMMATORY BOWEL DISEASE

(75) Inventor: Mark K. Wedel, Temecula, CA (US)

(73) Assignee: Atlantic Pharmaceuticals (Holdings) Limited, Essex (GB)

( * ) Notice: Subject to any disclaimer, the term of this patent is extended or adjusted under 35 U.S.C. 154(b) by 59 days.

(21) Appl. No.: 13/569,104

(22) Filed: Aug. 7, 2012

(65) Prior Publication Data

US 2013/0090368 A1 Apr. 11, 2013

Related U.S. Application Data

(63) Continuation of application No. 11/720,745, filed as application No. PCT/US2005/043611 on Dec. 2, 2005, now abandoned.

(60) Provisional application No. 60/632,826, filed on Dec. 2, 2004, provisional application No. 60/716,355, filed on Sep. 12, 2005.

(51) Int. Cl.
*A61K 31/70* (2006.01)
*C07H 21/02* (2006.01)
*C07H 21/04* (2006.01)
*A61K 31/7088* (2006.01)
*A61K 31/711* (2006.01)
*C12N 15/113* (2010.01)
*C12Q 1/68* (2006.01)
*A61K 31/7105* (2006.01)

(52) U.S. Cl.
CPC .......... *A61K 31/7088* (2013.01); *A61K 31/711* (2013.01); *A61K 31/7105* (2013.01); *C12N 15/1138* (2013.01); *C12N 2310/11* (2013.01); *C12N 2310/315* (2013.01)

(58) Field of Classification Search
None
See application file for complete search history.

(56) References Cited

U.S. PATENT DOCUMENTS

| | | | |
|---|---|---|---|
| 5,985,914 A | 11/1999 | Zeldis et al. | |
| 6,096,722 A | 8/2000 | Bennett et al. | |
| 6,747,014 B2 | 6/2004 | Teng et al. | |
| 6,930,093 B2 | 8/2005 | Brantl | |

OTHER PUBLICATIONS

Vegter et al. Alimentary Pharmacology and Therapeutics, pp. 1-10, 2013.*
Miner et al., "An enema formulation of Alicaforsen, an antisense inhibitor of intercellular adhesion molecule-1, in the treatment of chronic, unremitting pouchitis". Ailment. Pharmacol. Ther. Feb. 2004, 19:281-286.
Van Deventer et al., Gut. Nov. 2004, 53:1646-1651.
International Search Report for International Application PCT/US05/43611 dated Aug. 29, 2006.
"Phase II Study of Antisense Drug ISIS 2302 Demonstrates Significant and Long-Lasting Improvement of Symptoms in Patients With Ulcerative Colitis", Press Release, Isis Pharmaceuticals, Oct. 10, 2001.

* cited by examiner

*Primary Examiner* — Sean McGarry
(74) *Attorney, Agent, or Firm* — Knobbe, Martens, Olson & Bear, LLP

(57) ABSTRACT

Disclosed herein is a method for the sustained amelioration and/or treatment of ulcerative colitis comprising rectal administration of a compound comprising an antisense oligonucleotide having the sequence 5'-GCCCAAGCTG-GCATCCGTCA-3', ISIS 2302. The method results in a decrease in the indications of ulcerative colitis for an extended period (greater than 90 days) after the conclusion of the administration of the composition. The composition is well tolerated and systemic exposure is minimal.

23 Claims, No Drawings

THERAPEUTIC ANTISENSE OLIGONUCLEOTIDE COMPOSITIONS FOR THE TREATMENT OF INFLAMMATORY BOWEL DISEASE

RELATED APPLICATIONS

This application is a continuation of U.S. National Phase application Ser. No. 11/720,745, with a §371(c) date of Oct. 20, 2008, which is a U.S. national phase application under 35 U.S.C. §371 of International Application No. PCT/US2005/043611, filed Dec. 2, 2005, which claims priority under 35 U.S.C. §119(e) to U.S. Provisional Patent Application Nos. 60/632,826 filed on Dec. 2, 2004, and 60/716,355 filed on Sep. 12, 2005. All of which are incorporated herein by reference in their entirety.

SEQUENCE LISTING

A sequence listing is filed with this application under 37 CFR 1.821 and is hereby incorporated by reference.

FIELD OF THE INVENTION

This invention relates to antisense oligonucleotide therapeutic compound to modulate the expression of intracellular adhesion molecule-1 (ICAM-1) for the amelioration and/or treatment of inflammatory bowel diseases including Crohn's disease, ulcerative colitis and pouchitis.

BACKGROUND OF THE INVENTION

ICAM-1, a member of the immunoglobulin (Ig) superfamily, is an inducible transmembrane glycoprotein constitutively expressed at low levels on vascular endothelial cells and on a subset of leucocytes (Dustin et al., *J. Immunol.*, 137:245-54, 1986; Rothlein et al, *J. Immunol.*, 137:1270-4, 1986; Simmons et al, *Nature*, 331:624-7, 1988). The primary ligands for ICAM-1 binding are the $\beta_2$ integrins, LFA-1 and Mac-1, both of which are expressed on leukocytes (Marlin and Springer, *Cell*, 51:813-9, 1987; Diamond et al, *J. Cell Biol.*, 111:3129-39, 1990). ICAM-1 serves multiple functions in the propagation of inflammatory processes, the best characterized being the facilitation of leukocyte migration from the intravascular compartment to the extravascular space at sites of inflammation (Butcher, *Cell*, 67:1033-6, 1991; Furie et al, *Blood*, 78:2089-97, 1991; Oppenheimer-Marks et al., *J. Immunol.*, 147:2913-21, 1991). In addition, ICAM-1 also appears to provide an important second signal to T-lymphocytes during antigen presentation (Altmann et al., *Nature*, 338:512-4, 1989; Van Seventer et al., *J. ImmunoL* 144:4579-86, 1990; Kuhlman et al., *J. Immunol.*, 146:1773-82, 1991). It also plays and important faciliatory roll in cytotoxic T-cell (Makgoba et al., *Eur. J. Immunol.*, 18:637-40, 1988), natural killer cell (Allavena et al., *Blood*, 84:2261-8, 1994), and neutrophil-mediated (Ding et al., *J. Immunol*, 163:5029-38, 1999) damage to target cells.

In response to pro-inflammatory stimulators, including tumor necrosis factor-alpha (TNF-α) (To et al., *Arthritis Rheum.*, 39:467-77, 1996; Beutler, *Arthritis Rheum.*, 26:16-21, 1999), many cell types modulate the expression of ICAM-1 on their surface. Cellular adhesion molecules, including ICAM-1, are required for the migration of leukocytes and endothelial cells. Numerous studies have demonstrated an increase in ICAM-1 expression within involved tissues from patients suffering from a wide range of inflammatory diseases, including inflammatory bowel disease (IBD) (Jones et al., *Gut*, 36:724-30, 1995), rheumatoid arthritis (To et al., *Arthritis Rheum.*, 39:467-77, 1996), celiac disease (Sturgess et al., *Clin, Exp. Immunol.* 82:489-92, 1990), IgA neuropathy (Nguyen et al., *Am. J. Nephrol.* 19:495-9, 1999), systemic lupus (Papa et al., *Lupus*, 8:423-9, 1999; Egerer et al., *Lupus*, 9:614-21, 2000), inflammatory dermatosis (Ackermann et al., *Arch Dermatol Res.*, 290:353-9, 1998), and multiple sclerosis (Bo et al., *J. Neuropathol. Exp. Neurol.*, 55:1060-72, 1996).

Anti-ICAM-1 monoclonal antibodies have demonstrated beneficial effects in a variety of animal models of disease, including pulmonary inflammation and asthma (Barton et al., *J. Immunol.* 143:1278-82, 1989; Wegener et al., *Science*, 247: 456-9, 1990), allograft rejection (Cosimi et al., J. Immunol., 144:4604-12, 1990; Isobe et al., *Science*, 255:1125-7, 1993), nephritis (Flaming et al., *Clin. Immunol. Immunopath.*, 64:129-34, 1992; Kawasaki et al., *J. Immunol.*, 150:1074-83, 1993), ischemic injury (Ma et al., *Circulation*, 86:937-46, 1992; Kelly et al., *Proc. Natl. Acad. Sci., USA.* 91:812-6, 1994), inflammatory arthritis (Iigo et al., *J. Immunol.*, 147: 4167-71, 1991), contact dermatitis (Scheynius et al., *J. Immunol.* 150:655-63, 1993), and colitis (Hamamoto et al., *Clin. Exp. Immunol.*, 117:462-8, 1999). These animal models supported trials of inhibitors of either ICAM-1 function or expression in human disease.

ICAM-1 expression has been demonstrated during inflammatory bowel disease (IBD). In a mouse model of colitis induced by dextran sulfate, ICAM-1 expression is increased on the endothelium of colonic submucosal and tunica muscularis veins (Bennett, *J. Pharm. Exp. Ther.*, 280:988-1000, 1997). Human ICAM-1 expression in Crohn's disease is increased in the lamina propria micorovasculature (both colonic and jejunal) (Sousa et al., *Gut*, 45:856-63, 1999), gut mononuclear cells (Bernstein et al., *Clin. Immunopathol.*, 86:147-60, 1998), and apical portions of the colonic epithelium (Vanier et al., *Am. J. Surg. Pathol.*, 24:1115-24, 2000). Tissue expression of ICAM-1 correlates with disease activity (Vanier et al., *Clin. Exp. Immunol.*, 121:242-7, 2000).

Inflammatory bowel disease (IBD) refers to a group of diseases including both Crohn's disease and ulcerative colitis. The two diseases are often grouped together due to their similar pathogenesis and clinical manifestations. In the absence of invasive imaging studies, it is not possible to distinguish the two diseases which are often considered as a single disease in a number of publications and studies. Definitive diagnosis of either disease requires imaging studies such as endoscopy (either sigmoidoscopy or colonoscopy), double contrast barium enema, and computed tomography (CT) scan; combined with laboratory tests including complete blood counts to detect elevated leukocyte levels, erythrocyte sedimentation rates and serum albumin concentration.

Both diseases are chronic, relapsing/remitting inflammatory diseases of the gastrointenstinal (GI) tract. The regions of the GI tract that are most often affected by Crohn's disease are the small intestine and large intestine, also called the colon, including the rectum; however, Crohn's disease can affect the entire GI tract from the mouth to the anus. There may be single or multiple patches of inflammation. Ulcerative colitis affects only the large intestine. Inflammation and ulceration in ulcerative colitis are limited to the mucosal and submucosal layers, two innermost layers of the four layers of the large intestine. The inflammation and ulceration in Crohn's disease can extend through all layers of the intestinal wall in both the small and large intestines. Common symptoms of the diseases include diarrhea, abdominal pain, rectal bleeding and weight loss. Complications of Crohn's disease include intestinal abscesses, fistula, an abnormal passage leading from one portion of the intestine to another and permitting passage of fluids or secretions, and intestinal obstructions. Typically, the course of both diseases is intermittent, with disease exacerbations followed by periods of remission. However, ulcerative colitis may be a single event, or continuous with unrelenting symptoms.

Based on the overlap in the pathology and clinical manifestations, it is not surprising that available therapies for Crohn's disease and ulcerative colitis are substantially overlapping. A notable difference is the possibility of the use of enemas for the treatment of ulcerative colitis as the diseases areas are proximal to the rectum. This allows for topical application of a therapeutic agent. As Crohn's disease typically includes involvement of the small intestine, systemic treatment is typically required. Although there are many choices for therapeutic interventions in IBD, many have undesirable side effects that make them less than ideal for treatment of chronic disease.

For mild ulcerative colitis, orally or topically (i.e. enema) delivered aminosalicylates are typically the first line of treatment. The aminosalicylate class consists of agents that contain 5-aminosalicyclic acid (5-ASA), is one of the oldest anti-inflammatory compounds employed in IBD. For example, the 5-ASA sulfasalazine was developed in the 1930's for the treatment of rheumatoid arthritis, and its utility in the treatment of IBD was established in the 1970's (Anthonisen et al., *Scan. J. Gastroenterol.*, 9:549-554, 1974). Used in high doses, 5-ASAs can induce remission in acute attacks. Although commonly used for maintenance therapy, 5-ASAs have not been demonstrated to be effective in maintaining remission.

Commonly used 5-ASA formulations include sulfasalazine, oral and topical mesalamine, olsalazine and balsalazide. Various formulations are modified to provide available active drug to the site of interest (e.g. small or large intestine). Side effects are not uncommon with 5-ASAs. Sulfasalazine has a relatively high toxicity (approximately one third of patients), associated with the sulfa group, including headache, nausea, dyspepsia and anorexia. Less common side effects include fever, rash, arthralgia, hemolysis, neutropenia, exacerbation of colitis, hypersensitivity reactions and nephrotoxicity. Mesalamine, olsalazine and balsalazide which do not contain sulfa groups result in substantially fewer side effects, but still can cause rash, headaches and fever. Other more severe side effects have also been reported.

Mesalamine enema has been implicated in the production of an acute intolerance syndrome characterized by cramping, acute abdominal pain and bloody diarrhea, sometimes headache, fever and a rash. While using mesalamine enema, some patients have developed pancolitis; however, the frequency was lower than with a placebo treated group. The extent of absorption of mesalamine from enema is largely dependent on retention time and therefore varies. Systemic exposure is substantially reduced by enema administration as compared to oral administration; however, 10 to 30% of the daily dose can be recovered in 24-hour urine collection suggesting that the systemic exposure is not insubstantial. Under clinical conditions, patients demonstrate plasma levels of 2 ug/ml, about two thirds of which was the N-acetyl metabolite, at 10 to 12 hours post-administration. (*Physicians Desk Reference*, 53$^{rd}$ Edition. 1999. Medical Economics Data, Montvale, N.J., pp 3126-7)

Corticosteroids are among the most effective agents for inducing remission in IBD attacks and are typically the second therapeutic option upon failure of treatment with 5-ASAs. The compounds are delivered first either orally or rectally, with or without concomitant administration of 5-ASAs. Upon failure of oral delivery, the compounds are administered intravenously. Ideally, corticosteroids are used for only a short course of treatment and tapered off upon remission of disease.

Corticosteroids commonly used for the treatment of IBD include prednisone, budesonide and hydrocortisone. The use of corticosteroids is limited by the number of severe and significant side effects associated with their use. Common side effects of short term use include insomnia, night sweats, mood changes and altered glucose metabolism. Prolonged maintenance therapy is typically reserved only for severe, refractory cases. Prolonged therapy can lead to adrenal atrophy, whereas abrupt cessation can cause adrenal insufficiency, hypotension, and even death. Other side effects include acne, abnormal fat deposition, excessive hair growth and osteoporosis. In Crohn's disease, corticosteroids can thwart the healing of fistula, exacerbating the disease state.

Individuals responding to oral or rectal corticosteroids are often placed on a maintenance dose of 5-ASA. However, some physicians provide no pharmacological interventions during periods of remission. Individuals who require therapy with intravenous corticosteroids are typically maintained on an immunosuppressive agent such as 6-mercaptopurine and/or azathioprine, in combination with a 5-ASA. Parenteral nutrition is typically considered with such severe disease. When the patient does not respond to the above therapies, the immunosuppressant cyclosporine may be administered in an attempt to avoid surgery to remove the section of diseased intestine.

Immunosuppressant interventions are not without undesirable side effects. 6-Mercaptopurine and azathioprine can cause fever, rash, nausea and headache, with more severe side effects including leucopenia, pancreatitis, severe infections and bone marrow suppression. Cyclosporine can have more severe side effects including paresthesias (abnormal sensations like burning or tingling), excessive hair growth, hypertension, tremor, renal insufficiency, headache and opportunistic infections.

Antibiotics, typically ciprofloxacin or metronidazole, are used as add on therapies to 5-ASA or corticosteroids, especially with patients with fistulizing or colonic disease. As with all of the other therapies, there are side effects of long term treatment with antibiotics.

Infliximab is currently the pharmacotherapy of last resort in IBD. It is a chimeric monoclonal antibody composed of 75% human and 25% mouse protein. Infliximab is an inhibitor of tumor necrosis factor-alpha (TNF-$\alpha$), a potent inflammatory cytokine. The drug acts as a sink by binding both soluble and membrane bound TNF-$\alpha$. By inhibiting an activator high in the inflammatory cascade, a number of inflammatory pathways can be inhibited. The drug is administered intravenously first for treatment and subsequently as a maintenance drug every eight (8) weeks as indicated on the product label. However, as it is a biological agent, an immune response can limit utility of the drug. Therefore, immunosuppressive agents are typically given in conjunction with infliximab maintenance therapy. As with all other therapies for IBD, there are substantial side effects of infliximab. TNF-$\alpha$ plays an important role in the eradication of neoplastic cells; therefore, its suppression can lead to opportunistic infections, malignancies and other complications, especially as a long term strategy (Brown et al., *Arthritis Rheum.*, 46:3151-8, 2002; Lee et al., *Arthritis Rheum.*, 46:2565-70, 2002; Nahar et al., *Ann. Pharmacotherapy*, 37:1256-65, 2003).

Surgical interventions are a method of treatment of IBD, not a cure. Due to the chronic nature of IBD and the relatively early age of onset, multiple surgeries can be required over the lifetime of patients who are not responsive to pharmacological interventions. Removal of short portions of the intestine is possible without substantial side effects. However, removal of larger or multiple segments of the intestine can result in short bowel syndrome in which individuals are unable to absorb nutrients. Removal of portions of the large intestine can result in the need for colostomy or other further surgical procedures. Therefore, surgery is not a preferred method of treatment of IBD.

Surgical interventions for the treatment of IBD can result in further disease. Upon complete removal of the colon, an ileal pouch may be constructed from the small intestine by the surgeon to allow removal of feces through the anus rather than requiring a permanent ostomy. Pouchitis is a non-specific inflammation of the ileal pouch which typically occurs within the first two years after reconstruction. Symptoms include steadily increasing stool frequency that may be accompanied by incontinence, bleeding, fever and/or a feeling of urgency. Of those who have ulcerative colitis, approximately 20 to 30 percent experience at least one episode. Antibiotics can be sufficient to treat pouchitis; however, other more aggressive therapies similar to those used in IBD are required.

Antisense oligonucleotides offer an ideal solution to the problems encountered in prior art approaches. They can be designed to selectively inhibit expression of a given nucleic acid or protein, and avoid non-specific mechanisms of action by interacting with a nucleic acid target based on nucleotide sequence, allowing for the inhibition of a specific isoform of a family of similar protein structure or activity. A complete understanding of target mechanisms or macromolecular interactions is not needed to design specific inhibitors.

Human ICAM-1 is encoded by a 3.3-kb mRNA (SEQ ID NO 1) resulting in the synthesis of a 55,219 dalton protein. ICAM-1 is heavily glycosylated through N-linked glycosylation sites. The mature protein has an apparent molecular mass of 90 kDa as determined by SDS-polyacrylamide gel electrophoresis (Staunton et al., *Cell,* 52:925-933, 1988). ICAM-1 is a member of the immunoglobulin (Ig) superfamily. It contains five immunoglobulin-like domains at the amino terminus, followed by a transmembrane domain and a cytoplasmic domain. The primary binding site for LFA-1 and rhinovirus are found in the first immunoglobulin-like domain. However, the binding sites appear to be distinct (Staunton et al., *Cell,* 61:243-354, 1990).

ICAM-1 exhibits a broad tissue and cell distribution, and may be found on white blood cells, endothelial cells, fibroblast, keratinocytes and other epithelial cells. The expression of ICAM-1 can be regulated on vascular endothelial cells, fibroblasts, keratinocytes, astrocytes and several cell lines by treatment with bacterial lipopolysaccharide and cytokines such as interleukin-1, tumor necrosis factor, gamma-interferon, and lymphotoxin (See, e.g., Frohman et al., *J. Neuroimmunol.,* 23:117-124, 1989).

A series of oligonucleotides were tested for the ability to inhibit the expression of human ICAM-1 (SEQ ID NO 1) using both in vitro and in vivo experiments (see e.g., U.S. Pat. No. 5,514,788). From these experiments, the oligonucleotide ISIS 2302 (SEQ ID NO 2) which is targeted to nucleotides 2114 to 2133 of human ICAM-1 was selected for further development.

ISIS 2302 is a 20-base phosphorothioate oligodeoxynucleotide designed to specifically hybridize to a sequence in the 3'-untranslated region of the human ICAM-1 mRNA. Studies strongly suggest that ISIS 2302 functions by specifically binding to the ICAM-1 mRNA resulting in cleavage of the mRNA by the enzyme RNaseH1 (Crooke, *Biochim. Biophys. Acta.,* 1489:31-44, 1999), one of a ubiquitous family of RNaseH nucleases. However, the method of the invention is not limited by the mechanism of action of ISIS 2302.

Phosphorothioate modification of the oligodeoxynucleotide, by substituting a sulfur molecule for a non-bridging oxygen molecule in each phosphodiester linkage, significantly increases exonuclease resistance relative to unmodified DNA and prolongs the drug half life (Geary et al., *Anti-Cancer Drug Design,* 12:383-94, 1997). Phosphorothioate oligonucleotides are only minimally antigenic, non-cytotoxic and well tolerated, and their pharmacokinetic and pharmacodynamic properties are well characterized (see e.g., Butler et al., *Lab. Invest.,* 77:379-88, 1997; Mirabelli et al., *Anti-Cancer Drug Des.,* 6:647-61, 1991)

In addition to phosphorothioate backbone modifications, a number of other possible backbone, sugar and other modifications are well known to those skilled in the art and are discussed in the parent applications on which this application is based.

Antisense oligonucleotides targeted to ICAM were shown to be effective in mouse and rat models of inflammatory bowel disease when systemically administered by subcutaneous or intraperitoneal injection (see, e.g., Bennett, U.S. Pat. No. 5,514,788, example 20; and U.S. Pat. No. 6,096,722, example 29, respectively). These data were the foundation for the development of clinical trials for the treatment of Crohn's disease, pouchitis and ulcerative colitis in humans. In the Crohn's trial, ISIS 2302 (Alicaforsen) was administered systemically to individuals in placebo controlled studies. Phase II studies suggested efficacy of intravenously administered ISIS 2302 in some subsets of patients (Yacshyn et al., *Gut,* 51:30-36. 2002; Yacyshyn et al., *Aliment. Pharmacol. Ther.,* 16:1761-70. 2002). In two subsequent Phase III trials, intravenously administered ISIS 2302 was found to be ineffective in treating moderate to severe Crohn's disease patients based on clinical remission and disease activity index scores (Chey et al., *Gastroenterology,* 128:A-112, abst 724. 2002).

An enema formulation of ISIS 2302 was used in a clinical trial for the treatment of pouchitis (US Patent Publication 20040162259, see Example 17, Miner et al., *Alimnet. Pharmacol. Ther.,* 19:281-6.2004). Twelve patients with chronic, unremitting pouchitis and a Pouchitis Disease Activity Index (PDAI) of at least 7 were enrolled in the study. PDAI is a clinical score based on a combination of factors including stool frequency, rectal bleeding, fecal urgency, abdominal cramps, fever of greater than 100° F., endoscopic and histologicic scores. Traditionally, active pouchitis is defined as having a PDAI score of at least 7. Patients underwent a 6 week course of nightly administration of a hydroxypropyl methylcellulose enema containing 240 mg of ISIS 2302. Evaluations were performed at baseline and at weeks 3, 6, and 10. The primary endpoint of reduction of PDAI at week 6 was reached (p=0.001) with significant decreases in endoscopy and symptom scores seen as early as week 3, and continuing through week 6, with improvements seen in each of the endoscopy components through week 10. Clinical symptom scores also decreased from baseline to week 6. The enema was well tolerated and there were no serious adverse events in the study. No long term follow-up beyond the week 10 evaluation was performed.

A small randomized, controlled, double-blind escalating dose study of rectally delivered ISIS 2302 for the treatment of mild to moderate ulcerative colitis (SJH van Deventer et al., *Gut,* 53:1646-51). Patients were treated with one of four daily doses of ISIS 2302 (6, 30, 120 and 240 mg) for 28 days, and the safety and efficacy of the treatment were monitored after 1, 3 and 6 months for improvement in disease activity index (DAI). DAI is a clinical score based on stool frequency, rectal bleeding, endoscopic appearance and investigator's global assessment. None of the patients in the 240 mg/day group or compared with 50% of the patients in the placebo group required additional surgical or medical intervention over baseline during the six months of the study. The results showed promising acute and long term benefits; however, the results required verification in a larger clinical trial to be conclusive.

Despite a number of possible interventions for the treatment of IBD, none of them are fully satisfactory due to limited efficacy, undesirable side effects or both. There clearly remains an unmet need for effective treatment of IBD, preferably treatments that produce sustained effects due to the chronic nature of the disease.

SUMMARY OF THE INVENTION

Disclosed is a method for the sustained amelioration or treatment of ulcerative colitis comprising rectal administration of a therapeutic dose of a composition comprising an antisense oligonucleotide compound 8 to 80 nucleobases in length, preferably formulated in hydroxylpropyl methylcellulose, to an individual wherein the oligonucleotide comprises at least an 8 nucleobase portion that specifically hybridizes with nucleotides 2114 to 2133 of SEQ ID 1, and monitoring the individual for amelioration of disease. Further disclosed is a method for promoting mucosal healing and a durable response comprising administration of the composition. Further disclosed is a method for producing disease modifying results comprising administration of the composition. These methods accomplish their therapeutic endpoints with minimal systemic exposure to the active components of the composition and without substantial side effects. In a preferred embodiment, the method is used on individuals having moderate to severe ulcerative colitis.

Disclosed is a method for the sustained amelioration or treatment of ulcerative colitis comprising rectal administration of a therapeutic dose of a composition comprising an antisense oligonucleotide compound having the sequence (SEQ ID 2):

5'-GCCCAAGCTGGCATCCGTCA-3' in hydroxypropyl methylcellulose, wherein the oligonucleotide inhibits expression of the ICAM-1 protein, and monitoring the individual for amelioration of disease. Further disclosed is a method for promoting mucosal healing and a durable response comprising administration of the composition. Further disclosed is a method for producing disease modifying results comprising administration of the composition. These methods accomplish their therapeutic endpoints with minimal systemic exposure to the active components of the composition and without substantial side effects. In a preferred embodiment, the method is used for the treatment individuals having moderate to severe ulcerative colitis.

Disclosed is the use of composition comprising an antisense oligonucleotide compound 8 to 80 nucleobases in length wherein the oligonucleotide comprises at least an 8 nucleobase portion that specifically hybridizes with nucleotides 2114 to 2133 of SEQ ID NO: 1 for the preparation of a medicament for rectal administration to an individual to promote mucosal healing and a durable response in an individual suffering from ulcerative colitis. A further use for the medicament is to produce disease modifying outcomes. These uses can be accomplished with minimal systemic exposure to the active components of the composition and without substantial undesirable side effects. It is further disclosed that the oligonucleotide can have the sequence of SEQ ID NO: 2, and that the medicament for rectal administration can be prepared using hydroxypropyl methylcellulose. In a preferred embodiment, the composition is used for the manufacture of a medicament for the treatment of individuals having moderate to severe ulcerative colitis.

DETAILED DESCRIPTION OF THE INVENTION AND PREFERRED EMBODIMENTS

Antisense oligonucleotides hold great promise as therapeutic agents for the treatment of many human diseases. Oligonucleotides specifically bind to the complementary sequence of either pre-mRNA or mature mRNA, as defined by Watson-Crick base pairing, inhibiting the flow of genetic information from DNA to protein. The properties of antisense oligonucleotides that make them specific for their target sequence also make them extraordinarily versatile. Because antisense oligonucleotides are long chains of four monomeric units they may be readily synthesized for any target RNA sequence.

Methods delivery of pharmaceutical compositions such as those of the instant invention (e.g. oligonucleotides) are well known. In the instant invention, the oligonucleotide is delivered by rectal administration in an enema formulation comprising the oligonucleotide in hydroxypropyl methylcellulose. Details regarding routes of administration are provided in the subsequent examples and in the parent patent applications which are incorporated herein by reference Formulations for the delivery of pharmaceutical compositions are well known to those skilled in the art. The selection of a specific formulation is based on considerations well known to those skilled in the art including, but not limited to, route of administration, solubility of the compound to be administered and quantity of the compound to be administered. Detailed formulations are presented in the examples and in U.S. Pat. Nos. 6,096,722 and 6,747,014 both incorporated herein by reference.

The studies discussed below in the Examples demonstrate the efficacy and safety of ISIS 2302 in the amelioration and treatment of ulcerative colitis. ISIS 2302 produces a durable response that is more sustained than with the standard of care, mesalamine. This durability of response is critical in a disease such as ulcerative colitis that has a profound effect on the quality of life of individuals who suffer from the disease. By reducing the frequency of flares the quality of life of the patient is improved. Moreover, ISIS 2302 has been shown to have disease modifying activity which has not been observed with any previous therapies for ulcerative colitis.

The oligonucleotide tested in the trials disclosed herein had a fully phosphorothioate modified backbone. Other possible backbones, modified sugars or other forms of the same nucleotide sequence can be used in the instant invention.

DEFINITIONS

In the context of this invention, the term "oligonucleotide" refers to an oligomer or polymer of ribonucleic acid or deoxyribonucleic acid. This term includes oligomers consisting of naturally occurring bases, sugars and intersugar (backbone) linkages as well as oligomers having non-naturally occurring portions which function similarly. Such modified or substituted oligonucleotides are often preferred over native forms because of properties such as, for example, enhanced cellular uptake, increased stability in the presence of nucleases and increased hybridization affinity. Details regarding possible modifications of oligonucleotide backbones and sugars, including mixed or chimeric oligomers, are discussed extensively in both patent and non-patent publications and are well known to those skilled in the art. The use of oligomer mimetics such as peptide nucleic acids (PNA) and locked nucleic acids (LNA) to increase the affinity of an oligonucleotide for its target and provide tolerance for mismatches to the target sequence are well known to those skilled in the art. Methods for synthesis of unmodified and modified oligonucleotides are also provided. In preferred methods of the instant invention, oligonucleotides contain at least one phosphorothioate and/or heteroatom internucleoside linkage wherein a phosphorothioate linkage is most preferred.

The oligonucleotides in accordance with this invention preferably comprise from about 8 to about 80 nucleic acid base units. It is more preferred that such oligonucleotides comprise from about 12 to 50 nucleic acid base units, still more preferred to have from about 15 to 30 nucleic acid base units, and most preferred to have from about 18 to 22 nucleic acid base units. As will be appreciated, a nucleic acid base unit is a base-sugar combination suitably bound to an adjacent nucleic acid base unit through phosphodiester or other bonds. One skilled in the art will understand that about 8 to about 80 nucleic acid base units includes 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80 nucleobase units.

The oligonucleotide compound of the invention preferably comprise at least an 8 nucleobase portion, more preferably at least a 12 nucleobase portion, even more preferably at least an 15 nucleobase portion, further more preferably an 18 nucleobase portion, most preferably a 20 nucleobase portion that specifically hybridizes with nucleotides 2114 to 2133 of SEQ ID NO: 1.

"Inflammatory bowel disease" (IBD), in the context of the invention means diseases that cause irritation and ulcers in the intestinal tract, with the most common forms of IBD being Crohn's disease and ulcerative colitis. Other inflammatory bowel diseases include, but are not limited to pouchitis, irritable bowel syndrome, regional enteritis and regional ileitis.

"Messenger RNA" is understood by those skilled in the art to be the open reading frames (ORFs) of the DNA from which they are transcribed includes not only the information from the ORFs of the DNA, but also associated ribonucleotides which form regions known to such persons as the 5'-untranslated region, the 3'-untranslated region, and intervening sequence ribonucleotides. Thus, oligonucleotides may be formulated in accordance with this invention, which are targeted wholly or in part to these associated ribonucleotides as, well as to the informational ribonucleotides. In preferred embodiments, the oligonucleotide is specifically hybridizable with a sequence in the 3'-untranslated region, specifically nucleotides 2114 to 2133 of SEQ ID NO 1.

"Hybridization", in the context of this invention, means hydrogen bonding, which may be Watson-Crick, Hoogsteen, or reversed Hoogsteen hydrogen bonding, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them.

"Specifically hybridizable" and "complementary" are terms which are used to indicate a sufficient degree of complementarity such that stable and specific binding occurs between the DNA or RNA target and the oligonucleotide. An oligonucleotide is specifically hybridizable when binding of the oligonucleotide to the target interferes with the normal function of the target molecule to cause a loss of activity, and there is a sufficient degree of complementarity to avoid non-specific binding of the oligonucleotide to non-target nucleic acid sequences under conditions in which specific binding is desired, i.e., under physiological conditions in the case of in vivo assays or therapeutic treatment or, in the case of in vitro assays, under conditions in which the assays are conducted.

"Pharmaceutical composition" is a composition comprising a pharmacologically active agent optionally further containing a vehicle to deliver the agent wherein the composition is suitable for administration to an animal, preferably a human animal. The vehicle may be inert, such as normal saline or agent to make the composition more palatable in the case of an orally administered composition. The vehicle may alternatively be an active agent to increase or modify bioavailability of the pharmacologically active agent. Such active vehicles include penetration enhancers or compounds to protect the pharmacologically active in the stomach to allow the pharmacologically active agent to be absorbed in the intestine. Such active vehicles are known to those skilled in the art.

A "therapeutic dose" is a quantity of a composition required to provide amelioration or treatment of the disease to be treated by the composition. Methods for monitoring disease are well known to those skilled in the art. Guidance is provided in the examples regarding therapeutic doses and methods for monitoring the severity of disease, specifically IBD.

"Sustained" is a longer state of substantially reduced clinical manifestations of ulcerative colitis and/or a maintained level of mucosal healing after termination of administration of the compositions disclosed herein without the need for increased therapy using other pharmacological or surgical interventions as compared to the standard of care or placebo. Sustained is defined as at least about sixty (60) days, preferably at least about ninety (90) days, even more at least about preferably 120 days, most preferably at least about 180 days of reduced indications of the disease or level of mucosal healing beyond administration of the last dose of the composition disclosed herein. A sustained reduction in clinical manifestations is indicative of a more durable response to the intervention.

A drug with "disease modifying activity" as used herein means a composition with the ability to slow down the rate of progression of disease as defined by standard disease monitoring measures (e.g., DM), and/or to have effects for an extended period after the clearance of the drug.

"Indications of ulcerative colitis" are symptoms or conditions that are associated with the presence of the disease ulcerative colitis. The indications may be objective (e.g. number of stools, rectal bleeding, mucosal friability), subjective (e.g. physician's assessment) or a composite of multiple observations (e.g. DAI, or clinical activity index)

"Disease Activity Index (DAI)" for ulcerative colitis is defined by Schroeder et al. (1987. *N. Engl. J. Med.* 317:1625-9) and is an aggregate score based on stool frequency, rectal bleeding, endoscopic appearance and the investigator's global assessment which includes patient's symptoms, findings of sigmoidoscopy and physical examination, laboratory studies and the patient's overall status. Each of the four aspects of the index is rated from 0-3 with 0 being the least severe and 3 being the most severe.

A "treatment period" as used herein means a time during which the composition is administered on a relatively frequent basis, at least weekly. A treatment period is preferably at least twice weekly, more preferably every other day, most preferably daily, for at least about two weeks, preferably at least about three weeks, more preferably at least about four weeks.

"Minimal systemic exposure" as used herein means the systemically available dose being less than about 5%, preferably less than about 4%, more preferably less than about 3%, even more preferably less than about 2%, and most preferably less than about 1% of the administered dose.

Example 1

Analysis of Bioavailability of ISIS 2302 Following Intrajejunal and Rectal Administration of Formulations The absolute bioavailability of ISIS 2302 was assessed following intrajejunal instillation in several formulations. Percent bioavailability was calculated from the resulting data according to the following formula:

% Bioavailability=$(AUC_{po}/D_o)/(AUC_{iv}/D_o) \times 100$%, wherein $AUC_{po}$ is area under the plasma concentration curve for formulated oligonucleotide tablets administered orally, $AUC_{iv}$ is area under the plasma concentration curve for oligonucleotide administered as an i.v. solution (control), and $D_o$ is the respective dosages for these two regimens.

To determine the bioavailability of formulations of oligonucleotide drugs two different modes of administration were studied. The oligonucleotide was formulated in an water-in-oil emulsion prepared as follows. First, the two phases were prepared. The aqueous phase was prepared by mixing 2 ml of ISIS 2302 solution (100 mg/ml) and 2 ml of water. The oil phase was prepared by gently heating 1 g Grill 3 (sorbitan monostearate) (Croda, US), 3 ml Captex 355 (Abitec Corp., Janesville, Wis.), and 3 ml Labrasol (Gattefosse, France) to about 70° C. The aqueous solution was slowly poured into the oil phase with vigorous mixing.

For intrajejunal instillation, Sprague-Dawley rats weighing 250-300 g were used. After overnight fasting, the rats were anesthetized with 5% pentobarbital (50 mg/kg) by intraperitoneal injection. After a midline abdominal incision was made, the small intestine was pulled out and injection site was located (2 cm after the ligament of Treitz). An aliquot of 1.0 mL drug formulation was then injected via a 27 gauge needle. Muscle was then surgically closed and skin was clipped after injection.

For rectal administration, test rats were first administered a cleansing enema following a period of overnight fasting, and then dosed with a sample of the test formulation. The enema formulation was applied via a catheter and held for a period of 1 hour.

In order to assess bioavailability of oligonucleotide, samples are processed and the amount of oligonucleotide present assessed by capillary gel electrophoresis (CGE) and HPLC analyses.

The absolute bioavailability of ISIS 2302 was determined following intrajejunal instillation in five Sprague-Daley rats and following rectal administration in seven rats. For intrajejunally administered ISIS 2302, the absolute bioavailability was 20.3% (n=5). For rectally administered ISIS 2302, the absolute bioavailability was 24.5% (n=7).

Example 2

Preparation of Enema Formulations for Analysis of Tissue Uptake of Oligonucleotide To evaluate the delivery and mucosal penetration of oligonucleotides into the colon following rectal delivery, the following formulations were prepared (Table 1). Solution and emulsion formulations of ISIS 2302 were prepared. Additives used in the formulations included saline, hydroxypropyl methyl cellulose (HPMC), carrageenan, Vitamin E a-tocopheryl polyethyelene glycol 1000 succinate (TPGS), Tween 80 and sorbitol.

Formulation 1a: A solution of ISIS 2302 was prepared in sterile saline at the desired concentration and used for in vivo evaluation.

Formulation 1b: A solution of ISIS 2302 and hydroxypropyl methyl cellulose (HPMC) was prepared such that the final concentration of ISIS 2302 was identical to that in Formulation 2a and the concentration of HPMC was 1.5%.

Formulation 1c: A solution of ISIS 2302 was prepared, as for Formulation 2a, containing 1.0% carrageenan and 2.5% Vitamin E TPGS.

Formulation 1d: A water-in-oil emulsion of ISIS 2302 was prepared following the general methods in the above example.

Formulation 1e: This formulation was prepared by mixing ISIS 2302, Tween 80 and HPMC in the appropriate quantities so as to afford a mixture that had the desired concentration of ISIS 2302, 0.5% Tween 80 and 0.75% HPMC.

Formulation 1f: This formulation was prepared by mixing ISIS 2302, Sorbitol and HPMC in the appropriate quantities so as to afford a mixture that had the desired concentration of ISIS 2302, 5% Tween 80 and 0.75% HPMC.

TABLE 1

ISIS 2302 formulations for topical/enema administration

| Formulation | Composition |
| --- | --- |
| 1a | ISIS 2302 in Saline |
| 1b | ISIS 2302 + 1.5% Hydroxypropyl Methyl Cellulose (HPMC) |
| 1c | ISIS 2302 + 1.0% Carrageenan + 2.5% Vitamin E a-Tocopheryl Polyethylene Glycol 1000 Succinate (TPGS) |
| 1d | ISIS 2302 in a water-in-oil emulsion |
| 1e | ISIS 2302 + 0.5% Tween 80 + 0.75% HPMC |
| 1f | ISIS 2302 + 5% Sorbitol + 0.75% HPMC |

Formulations of oligonucleotide were evaluated via rectal administration as enemas to laboratory beagle dogs. Following a period of overnight fasting, test dogs were first administered a cleansing enema and then dosed with a sample of the test formulation. The enema formulation was applied via a Foley catheter and held for a period of 1 h. In order to assess colonic tissue delivery and uptake of oligonucleotide, colon tissue biopsies were performed on the test animal, 3 h and 24 h after dosing. Tissue samples were processed and the amount of oligonucleotide present in the tissue assessed by capillary gel electrophoresis (CGE) and immunohistochemical (IHC) analyses.

Six formulations of ISIS 2302 as prepared in the previous example (Formulations 2a-2f) were administered to dogs via rectal enemas and the local distribution of ISIS 2302 in colonic tissue was determined by CGE and IHC at 3 h and 24 h following dosing. Results are shown in Table 2. It is notable that hydroxypropyl methylcellulose (1b) resulted in higher tissue uptake than the water-in-oil emulsion (1d) prepared by the method of Example 1 above.

TABLE 2

Local Colonic Tissue Distribution of ISIS
2302 Following Rectal Enema in Dog

| Formulation | Immunohistochemistry | | CGE (mg/g) ± SD | |
| --- | --- | --- | --- | --- |
| | 3 h | 24 h | 3 h | 24 h |
| 1a | ++++ | – | 782.2 ± 664.2 | NA |
| 1b | ++++ | – | 660.4 ± 439.6 | 6.8 ± 5.0 |
| 1c | ++++ | – | 557.8 ± 212.2 | 2.5 ± 1.4 |
| 1d | ++++ | – | 224.1 ± 78.3 | 1.2 ± 0.7 |
| 1e | ++++ | – | 620.7 ± 368.1 | 6.0 ± 5.9 |
| 1f | ++++ | – | | |

"++++" indicates strong immunohistochemical staining using a primary antibody to ISIS 2302; "–" indicates no significant staining compared to background levels.

Example 3

Analysis of Toxicity and Pharmacokinetics of Intravenously Administered ISIS 2302 in Humans in a Phase I Clinical Trial The first clinical trial with ISIS 2302 was to assess the safety and pharmacokinetics of intravenous administration of an anti-ICAM-1 antisense oligodeoxynucleotide in healthy subjects before commencing pilot therapeutic trials in target disease states. This was a double-blind, placebo-controlled, randomized (3:1, drug: placebo) study. Four healthy male volunteers were enrolled in each of seven single dose (0.06, 0.12, 0.24, 0.5, 1.0, 1.5 and 2.0 mg/kg) and multiple dose groups (0.2, 0.5, 1.0 and 2.0 mg/kg every other day for four doses). Groups were studied in a rising-dose fashion, and multiple dosing commenced after the first five single groups had completed the trial. ISIS 2302 (or sterile normal saline as placebo) was administered by intravenous infusion in a volume of 80 ml over two hours. Subjects remained recumbent, with continuous ECG monitoring for four hours after the beginning of each infusion. Before and at intervals after each infusion, supine blood pressure and pulse, clotting screen including aPTT, thrombin time, prothrombin time, serum complement split products C3a and C5a, neutrophil count, urine microproteins, and standard laboratory safety screen (hematology, blood biochemistry and urinalysis) were measured. Serum samples were collected from multiple dose groups at 14 and 21 days after the last infusion to be analyzed for the presence of antibodies to ISIS 2302. Blood samples were taken for measurements of plasma concentration of ISIS 2302 before and up to 24 hours after the beginning of infusion.

Complement split products were measured by commercially available C3a and C5a assay kits (Amersham). Plasma was examined for the presence of anti-ISIS 2302 antibodies using a modification of a previously described ELISA methodology (Lacy and Voss, *J. Immunol. Methods*, 116:87-98, 1989). Medium from a hybridoma cell line producing monoclonal antibodies which recognize ISIS 2302 served as a positive control. The cell line was produced by immunizing mice with ISIS 2302 conjugated to keyhole limpet hemocyanin as ISIS 2302 does not appear to be immunogenic in mice.

Drug analysis was performed by capillary gel electrophoresis (CGE) as described by Leeds et al. (*Anal. Biochem.,* 235:36-43, 1996). A phosphorothioate standard oligonucleotide composed of 27 thymidine nucleotides (T27) was added to both plasma and urine as an internal standard. The linear range of concentrations of oligonucleotides detectable in plasma using this method was 10 nM to 20 µM (approximately 0.07 to 140 µg/ml).

During two-hour single infusions of ISIS 2302, metabolites co-migrating with synthesized n-1, n-2 and n-3 chain-shortened forms of the intact drug appeared rapidly in plasma, constituting 20% of total oligonucleotide after 30 minutes of infusion. Interestingly, the relative proportion of total oligonucleotide constituted by full length drug, n-1, n-2 and n-3 forms remained relatively constant during the two hours of infusion and for at least the four additional hours post-infusion during which metabolites could be measured. Intact drug therefore constituted the majority of oligonucleotide present at all times at which drug or metabolites were detectable.

Urine samples from the 1.0 and 2.0 mg/kg multiple dose groups were analyzed for concentrations of intact drug and metabolites. Although very low concentrations of drug or metabolites were excreted in urine (less than 0.5% of the total drug administered was excreted in the first six hours), intact drug and n-1, n-2 and n-3 forms could be measured, and the quantity of shorter forms could be estimated from electropherograms. The amount of intact drug excreted over six hours after the beginning of infusion averaged approximately 0.05% of the administered dose, and the estimated total excretion of parent drug and metabolites in this time period was less than 0.5% of the total dose.

Example 4

Analysis of Toxicity and Pharmacokinetics of Subcutaneously Administered ISIS 2302 in Humans in a Phase I Trial A Phase 1 study of subcutaneously administered ISIS 2302 was conducted in normal volunteers. In the first phase of the study, the tolerability and pharmacokinetics of a single 1 ml subcutaneous injection of ISIS 2302 at concentrations ranging from 50-200 mg/ml were administered in double-blinded, placebo controlled, randomized (3:1; study drug:placebo) fashion to cohorts of four subjects. All concentrations produced mild injection site erythema, edema and induration that lasted for a few days. This was more of a clinical observation than a patient complaint, and it appeared that all doses were adequately tolerated. Preliminary analysis indicates that plasma bioavailability appears to be about 50%, with a time to maximal concentration of 1-3 hours. Regimens of 1 mg/kg every other day for 4 doses or weekly for 4 weeks were marginally tolerated, with evidence of very low grade complement activation (C3a only and not C5a) and low grade lymphadenopathy in addition to the mild injection site reactions described above. A 2 mg/kg bolus regimen was not well tolerated.

Example 5

Analysis of the Relative Absorption and Pharmacological Activity of ISIS 2302 Enema in the Treatment of Mild to Moderate Ulcerative Colitis in an Open Label Study (CS-28) The relative absorption (local and systemic pharmacokinetics) and pharmacological activity of ISIS 2302 enema was assessed in an open label study.

A population of 15 patients with mild to moderate active left sided ulcerative colitis (DIA 3-10) with mucosal friability were studied.

Patients were given 240 mg of ISIS 2302 enema nightly for six weeks. Endoscopic mucosal biopsy samples were taken at baseline and at the end of therapy. Intensive 24-hour plasma pharmacokinetic (PK) sampling was conducted on all patients after the first and last enema dose for quantitative drug analysis. End of treatment colonic biopsy samples were collected for local quantitative PK evaluation from the descending colon. Colonic tissue biopsies and timed plasma samples were assayed for drug concentration using a sensitive and selective hybridization ELISA bioanalytical method.

PK and clinical data from the first 12 patients were analyzed. Maximum plasma concentrations ($C_{max}$) ranged from 2.2 ng/mL to 38 ng/mL with the average time to maximum plasma concentration of 1.8 hr following the first enema. Mean AUC was 0.124 µg*hr/mL, indicating that less than 1% of the administered dose was systemically available. There were no differences in plasma PK values following a single dose compared with steady state doses at the end of the study. In contrast, colonic mucosal tissue concentrations of the parent oligonucleotide averaged 4300 ng/g wet tissue. Local tissue exposure was 100-fold higher than maximum drug concentrations observed in plasma. In a population with intestinal inflammation, friability and potential spontaneous bleeding, this low systemic exposure was surprising. Confinement of the drug to the specific region to be treated potentially increases safety and efficacy of the compound.

The disease activity index (DAI) significantly improved from baseline to week 6 in 9 of 12 patients. All patients entering the study had moderate to severe mucosal disease at baseline (modified Mayo score, endoscopic appearance component of DAI, of 2 or greater at baseline). Seven of 12 patients demonstrated mucosal healing and resolution of friability (modified Mayo score of 0 or 1) at the completion of the study. This was substantially higher than expected. Correlation of mucosal drug concentration and clinical response could not be demonstrated, but the clinical response parallels the efficacy of blinded trials.

Steady state and single dose systemic availability of ISIS 2302enemas is minimal in patients with active colonic inflammation. Effective tissue concentration of alicaforsen was achieved. A relationship between mucosal tissue concentration of alicaforsen and clinical response could not be established in this small cohort of patients.

Example 6

Analysis of the Safety and Efficacy of ISIS 2302 Enema in the Treatment of Mild to Moderate Ulcerative Colitis The safety and efficacy of four different dosing regimens of ISIS 2302 enema was assessed for the treatment of ulcerative colitis were analyzed in a placebo-controlled, double-blinded Phase 2 study.

A population of 112 patients with mild to moderate active distal ulcerative colitis (DIA 4-10) on stable background dose of oral mesalamine for 30 days prior to baseline visit, and/or stable background 6-mercaptopurine for 60 days prior to baseline visit, no TNF-α inhibitors, methotrexate, cyclosporine or thalidomide within 90 days of baseline visit was identified. Patient baseline characteristics were as follows: mean age 47.1 year, gender M/F: 67/45, mean disease duration 7.5 years, mean baseline DAI 6.9. Baseline characteristics were similar between the study groups. Patients were equally randomized into one of five study arms.

1. 240 mg ISIS 2302 nightly for six weeks.
2. 240 mg ISIS 2302 for 10 consecutive nights followed by 240 mg ISIS 2302 every other night for remaining 32 nights.
3. 240 mg of ISIS 2302 every other night for six weeks.
4. 120 mg of ISIS 2302 for 10 consecutive nights followed by 120 mg of ISIS 2302 every other night for the remaining 32 nights.
5. Placebo enema nightly for six weeks.

All patients received either a placebo enema or ISIS 2302 enema nightly for six weeks. Patients in arms 2 and 4 received placebo enemas on alternate nights when ISIS 2302 was administered on alternate days.

Primary response end point was a reduction in DAI at 6 weeks with secondary response being acute response, improvement/mucosal healing, remission and relapse.

Patients were followed for safety and efficacy through week 30, unless relapse, new medical or surgical intervention, or discontinuation of study medication occurred, in which case patients were monitored for safety for 30 days from last medication.

ISIS 2302 (Alicaforsen) 240 mg given nightly had a demonstrated significantly better response rate than placebo at weeks 18 and 30 (p=0.04 and 0.03). The 3 lower dose groups of alicaforsen failed to demonstrate statistical improvement over placebo. When subset analyses that included only the moderate disease group (DAI 8-10), or subjects with "true" left sided disease (15-40 cm) was performed the statistical differences were more pronounced and even significant at other time points (see Example 8).

Individual components of DAI were also analyzed. A durable reduction in stool frequency and rectal bleeding were observed in response to treatment with ISIS 2302.

The durability of the response to treatment was substantial. Of the subjects who initially achieved remission after 6 weeks of treatment, 10 of 13 subjects in the ISIS 2302 240 mg group remained in remission at week 30 (end of study) vs 4 of 9 in the placebo group (p=0.12). Thus the median duration of response for the ISIS 2302 240 mg group was significantly prolonged (≥6 months for treatment group vs <3 months for placebo).

ISIS 2302 240 mg given nightly for 6 weeks demonstrated statistically significant activity and durability of response, disease modifying activity, and was well generally well tolerated.

Example 7

Analysis of the Safety and Efficacy of ISIS 2302 Enema in the Treatment of Mild to Moderate Ulcerative Colitis The safety and efficacy of ISIS 2302 in a hydroxypropylmethylcellulose formulation was assessed for the treatment of patients with active mild to moderate active ulcerative colitis, left-sided colitis or pancolitis with left sided disease flare in a multicenter, randomized, double-blind, placebo controlled, dose ranging Phase 2 study.

A population of 191 patients with active, distal ulcerative colitis or pancolitis with left-sided disease flare and DAI scores of 4-10, on stable background dose of oral mesalamine for 30 days prior to baseline visit, and/or stable background 6-mercaptopurine for 60 days prior to baseline visit, no TNF-α inhibitors, methotrexate, cyclosporine or thalidomide within 90 days of baseline visit was identified. Patient baseline characteristics were as follows: mean age 45.3 year, gender M/F: 86/73, mean duration of disease 9.3 years, mean baseline DAI 7.3. Baseline characteristics were similar between study groups. Patients were equally randomized into three groups for treatment with either 120 mg of ISIS 2302, 240 mg ISIS 2302 or 4.0 g mesalamine, a common treatment for mild to moderate ulcerative colitis, in enema formulations. The formulations were administered nightly for six weeks.

The ISIS 2302 doses were selected for because they showed statistically significant efficacy in initial Phase 2 dose ranging studies. The doses were predicted on the basis of animal studies to yield local tissue concentrations shown to be effective in animal pharmacology models for inflammatory bowel disease. The primary response endpoint was a reduction in DAI at 6 weeks with secondary responses being acute response, improvement/mucosal healing, remission and relapse.

Patients were followed for safety and efficacy for 30 weeks unless relapse, new medical or surgical intervention or discontinuation of study medication in which case patients were monitored for safety for 30 days from the last study medication. Those patients not requiring additional or alternative medical or surgical interventions by week 30 were followed for safety and efficacy through week 24. Blood samples were drawn for plasma drug concentration measurements were taken at specified intervals for 24 hours after the first enema administration, and at weeks 3 and 6 in a subpopulation of 10 patients per treatment group.

The clinical response rates between the ISIS 2302 240 mg and mesalamine enemas were comparable throughout the study and both were superior to the ISIS 2302 120 mg enema. As can be seen in Table 3, the acute response to ISIS 2302 and mesalamine is similar; however, the response to ISIS 2302 is substantially more durable and sustained as determined by percent reduction in DAI, physician's assessment, maintenance of clinical remission and mucosal healing.

TABLE 3

Response to treatment with ISIS 2302 vs. Mesalamine

| | Mean % Δ in DAI from baseline | | | | |
|---|---|---|---|---|---|
| | Wk 6 | Wk 12 | Wk 18 | Wk 30 | Wk 54 |
| Mesalaimine (4 g) | −49.6 | −40.0 | −39.3 | −33.1 | −75.0 |
| ISIS 2302 (240 mg) | −47.1 | −56.3 | −61.5 | −46.9 | −85.7 |

Of the subjects who initially responded after 6 weeks of dosing, the median duration of response for ISIS 2302 240 mg approached 6 months where as the mesalamine enema was <3 months (p=0.20). Clinical remission rate at week 18 in the ISIS 2302 240 mg group was 20% vs 5.6% in the mesalamine treatment group (p=0.03). This trend was evident at all other time points throughout the study. No treatment related serious adverse events were reported in any study groups. SAES and AEs were comparable among study groups.

ISIS 2302 240 mg enema demonstrated activity similar to mesalamine enema in the acute left sided UC. However, subjects treated with ISIS 2302 240 mg trended toward a higher remission rate and a longer duration of remission than mesalamine. ISIS 2302 was well generally well tolerated.

Example 8

Analysis of Safety and Efficacy of ISIS 2302 Enema in the Treatment of Moderate to Severe Ulcerative Colitis An analysis of a subset of the population (n=26) of the study with moderate to severe disease was performed. Moderate to severe disease was defined as patients having the following scores using the DAI criteria: baseline stool frequency ≥2, rectal bleeding ≥2, endoscopy ≥2, and investigator's assessment ≥1. This subset population showed a substantial decrease in DAI as compared to both baseline and placebo in some of the treatment groups. Individuals receiving ISIS 2302 nightly had a significant (p≤0.05) decrease in DAI through week 18 of the study, and a strong trend (p≤0.09) towards a decrease in DAI throughout the remainder of the study. Similarly, individuals receiving ISIS 2302 every other night showed a significant (p≤0.05) decrease in DAI through week 6, and a strong trend (p≤0.11) towards a decrease in DAI at weeks 18 and 30. This subset analysis demonstrates the efficacy of ISIS 2302 in the treatment of moderate to severe ulcerative colitis. The analysis also demonstrates the disease modifying activity of ISIS 2302 by promoting sustained clinical remission in individuals with more severe disease.

What is claimed is:

1. A method for sustained amelioration of at least one indication of ulcerative colitis in an individual comprising:
   selecting an individual having moderate to severe ulcerative colitis; and
   rectally administering, at a frequency of once a day for at least 4 weeks, a therapeutic dose of a composition comprising an antisense oligonucleotide 15 to 30 nucleic acid base units in length to the individual, wherein the oligonucleotide comprises an at least 12 contiguous nucleobase portion that specifically hybridizes with nucleotides 2114 to 2133 of SEQ ID 1.

2. The method of claim 1, wherein the indication of ulcerative colitis comprises mucosal friability.

3. The method of claim 1, wherein the indication of ulcerative colitis comprises stool frequency.

4. The method of claim 1, wherein the indication of ulcerative colitis comprises rectal bleeding.

5. The method of claim 1, wherein the indication of ulcerative colitis comprises disease activity index.

6. The method of claim 1, wherein the antisense oligonucleotide is modified.

7. The method of claim 6, wherein the antisense oligonucleotide comprises at least one phosphorothioate nucleotide linkage.

8. The method of claim 6, wherein the antisense oligonucleotide comprises exclusively phosphorothioate nucleotide linkages.

9. The method of claim 1, wherein sustained amelioration of ulcerative colitis comprises amelioration of at least one indication of ulcerative colitis after termination of a treatment period of administration of the composition to the individual for at least 60 days.

10. The method of claim 1, wherein sustained amelioration of ulcerative colitis comprises amelioration of at least one indication of ulcerative colitis after termination of a treatment period of administration of the composition to the individual for at least 90 days.

11. The method of claim 1, wherein the rectally administered composition is an enema.

12. The method of claim 1, wherein the therapeutic dose comprises at least about 240 mg of the antisense oligonucleotide per administration.

13. The method of claim 1, wherein the oligonucleotide is about 18 to 22 nucleic acid base units in length.

14. The method of claim 1, wherein the composition further comprises hydroxypropyl methylcellulose.

15. The method of claim 14, wherein systemic exposure to the oligonucleotide is less than 5% of the dose administered.

16. The method of claim 1, wherein the composition is administered at a frequency of once a day for at least 6 weeks.

17. A method for sustained amelioration of at least one indication of ulcerative colitis in an individual comprising:
   selecting an individual having moderate to severe ulcerative colitis; and
   rectally administering an enema comprising 240 mg of ISIS 2302 to the individual at a frequency of once a day for 6 weeks.

18. The method of claim 1, wherein selecting the individual further comprises selecting an individual having left-side colonic spread of 5-40 cm in addition to having moderate to severe ulcerative colitis.

19. The method of claim 17, wherein selecting the individual further comprises selecting an individual having left-side colonic spread of 5-40 cm in addition to having moderate to severe ulcerative colitis.

20. The method of claim 1, wherein selecting the individual further comprises selecting an individual having moderate to severe ulcerative colitis who has failed a first line therapy for ulcerative colitis.

21. The method of claim 20, wherein the first line therapy for ulcerative colitis is mesalamine.

22. The method of claim 1, wherein the individual has severe ulcerative colitis and does not have mild to moderate ulcerative colitis.

23. The method of claim 22, wherein the individual has a ulcerative colitis disease activity index from 9 to 12.

* * * * *

SEQUENCE LISTING

<160> NUMBER OF SEQ ID NOS: 2

<210> SEQ ID NO 1
<211> LENGTH: 3025
<212> TYPE: DNA
<213> ORGANISM: H. sapien
<220> FEATURE:

<400> SEQUENCE: 1

```
gctataaagg atcacgcgcc ccagtcgacg ctgagctcct ctgctactca gagttgcaac      60
ctcagcctcg ctatggctcc cagcagcccc cggcccgcgc tgcccgcact cctggtcctg     120
ctcggggctc tgttcccagg acctggcaat gcccagacat ctgtgtcccc ctcaaaagtc     180
atcctgcccc ggggaggctc cgtgctggtg acatgcagca cctcctgtga ccagcccaag     240
ttgttgggca tagagacccc gttgcctaaa aaggagttgc tcctgcctgg gaacaaccgg     300
aaggtgtatg aactgagcaa tgtgcaagaa gatagccaac caatgtgcta ttcaaactgc     360
cctgatgggc agtcaacagc taaaaccttc ctcaccgtgt actggactcc agaacgggtg     420
gaactggcac ccctccctc ttggcagcca gtgggcaaga accttaccct acgctgccag     480
```

```
gtggagggtg gggcaccccg ggccaacctc accgtggtgc tgctccgtgg ggagaaggag    540
ctgaaacggg agccagctgt gggggagccc gctgaggtca cgaccacggt gctggtgagg    600
agagatcacc atggagccaa tttctcgtgc cgcactgaac tggacctgcg gccccaaggg    660
ctggagctgt tgagaacac ctcggccccc taccagctcc agacctttgt cctgccagcg    720
actcccccac aacttgtcag ccccegggtc ctagaggtgg acacgcaggg gaccgtggtc    780
tgttccctgg acgggctgtt cccagtctcg gaggcccagg tccacctggc actggggggac   840 cagaggttga accccacagt cacctatggc aacgactcct tctcggccaa ggcctcagtc    900
agtgtgaccg cagaggacga gggcacccag cggctgacgt gtgcagtaat actggggaac    960
cagagccagg agacactgca gacagtgacc atctacagct tccggcgcc aacgtgatt     1020 ctgacgaagc cagaggtctc agaagggacc gaggtgacga tgaagtgtga ggcccaccct   1080
agagccaagg tgacgctgaa tggggttcca gcccagccac tgggcccgag gcccagctc    1140 ctgctgaagg ccaccccaga ggacaacggg cgcagcttct cctgctctgc aaccctggag   1200
gtggccggcc agcttataca caagaaccag accggggagc ttcgtgtcct gtatggcccc   1260
cgactggacg agagggattg tccgggaaac tggacgtggc cagaaaattc ccagcagact   1320
ccaatgtgcc aggcttgggg gaacccattg cccgagctca gtgtctaaa ggatggcact    1380 ttcccactgc ccatcgggga atcagtgact gtcactcgag atcttgaggg cacctacctc   1440
tgtcgggcca ggagcactca aggggaggtc acccgcaagg tgaccgtgaa tgtgctctcc   1500
ccccggtatg agattgtcat catcactgtg gtagcagccg cagtcataat gggcactgca   1560
ggcctcagca cgtacctcta taaccgccag cggaagatca agaaatacag actacaacag   1620
gcccaaaaag ggaccccccat gaaaccgaac acacaagcca cgcctccctg aacctatccc   1680
gggacagggc ctcttcctcg gccttcccat attggtggca gtggtgccac actgaacaga   1740
gtggaagaca tatgccatgc agctacacct accggccctg ggacgccgga ggacagggca   1800
ttgtcctcag tcagatacaa cagcatttgg ggccatggta cctgcacacc taaaacacta   1860
ggccacgcat ctgatctgta gtcacatgac taagccaaga ggaaggagca agactcaaga   1920
catgattgat ggatgttaaa gtctagcctg atgagagggg aagtggtggg ggagacatag   1980
ccccaccatg aggacataca actgggaaat actgaaactt gctgcctatt gggtatgctg   2040
aggccccaca gacttacaga agaagtggcc ctccatagac atgtgtagca tcaaaacaca   2100
aaggcccaca cttcctgacg gatgccagct tgggcactgc tgtctactga ccccaaccct   2160
tgatgatatg tatttattca tttgttattt taccagctat ttattgagtg tcttttatgt   2220
aggctaaatg aacataggtc tctggcctca cggagctccc agtcctaatc acattcaagg   2280
tcaccaggta cagttgtaca ggttgtacac tgcaggagag tgcctggcaa aaagatcaaa   2340
tggggctggg acttctcatt ggccaacctg cctttcccca aaggagtga ttttctatc     2400 ggcacaaaag cactatatgg actggtaatg gttacaggtt cagagattac ccagtgaggc   2460
cttattcctc ccttcccccc aaaactgaca cctttgttag ccacctcccc acccacatac   2520
atttctgcca gtgttcacaa tgacactcag cggtcatgtc tggacatgag tgcccaggga   2580
atatgcccaa gctatgcctt gtcctcttgt cctgtttgca tttcactggg agcttgcact   2640
atgcagctcc agtttcctgc agtgatcagg gtcctgcaag cagtggggaa ggggggccaag  2700 gtattggagg actccctccc agctttggaa gcctcatccg cgtgtgtgtg tgtgtgtatg   2760
tgtagacaag ctctcgctct gtcacccagg ctggagtgca gtggtgcaat catggttcac   2820
```

-continued

```
tgcagtcttg accttttgag ctcaagtgat cctcccacct cagcctcctg agtagctggg    2880
accataggct cacaacacca cacctggcaa atttgatttt ttttttttttt ccagagacgg   2940 ggtcttgcaa cattgcccag acttcctttg tgttagttaa taaagctttc tcaactgcca   3000
aaaaaaaaaa aaaaaaaaaa aaaaa                                         3025

<210> SEQ ID NO 2
<211> LENGTH: 20
<212> TYPE: DNA
<213> ORGANISM: Artificial Sequence
<220> FEATURE:
<223> OTHER INFORMATION: Antisense Compound

<400> SEQUENCE: 2
gcccaagctg gcatccgtca                                               20
```